(12) United States Patent
Liu et al.

(10) Patent No.: US 11,618,909 B2
(45) Date of Patent: Apr. 4, 2023

(54) **ACID-TOLERANT *SACCHAROMYCES CEREVISIAE* AND USE THEREOF**

(71) Applicant: JIANGNAN UNIVERSITY, Wuxi (CN)

(72) Inventors: Long Liu, Wuxi (CN); Jian Chen, Wuxi (CN); Guocheng Du, Wuxi (CN); Jianghua Li, Wuxi (CN); Xueqin Lv, Wuxi (CN); Li Sun, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 237 days.

(21) Appl. No.: 17/118,532

(22) Filed: Dec. 10, 2020

(65) Prior Publication Data
US 2022/0002765 A1    Jan. 6, 2022

(30) Foreign Application Priority Data

Jul. 3, 2020 (CN) .......................... 202010631510.4

(51) Int. Cl.
*C12P 7/46* (2006.01)
*C12N 1/14* (2006.01)
*C12N 1/18* (2006.01)
*C12R 1/865* (2006.01)

(52) U.S. Cl.
CPC .................. *C12P 7/46* (2013.01); *C12N 1/14* (2013.01); *C12N 1/185* (2021.05); *C12R 2001/865* (2021.05)

(58) Field of Classification Search
CPC . C12N 1/14; C12N 1/18; C12N 1/185; C12N 1/36; C12P 17/04; C12P 7/42; C12P 7/46; C12P 7/48; C12P 7/56; C12P 7/58; C12R 2001/865
See application file for complete search history.

(56) References Cited

U.S. PATENT DOCUMENTS

| 5,270,190 A * | 12/1993 | Nakayama ................ C12P 7/46 435/232 |
| 2011/0045559 A1* | 2/2011 | Winkler .................... C12P 7/46 435/254.2 |
| 2011/0053233 A1* | 3/2011 | Brown ................... C07K 14/38 435/254.9 |

* cited by examiner

*Primary Examiner* — Blaine Lankford
(74) *Attorney, Agent, or Firm* — SZDC Law P.C.

(57) ABSTRACT

The present invention provides an acid-tolerant *Saccharomyces cerevisiae* strain and use thereof. By using exogenously added malic acid as a stress, an acid-tolerant mutant *S. cerevisiae* strain MTPfo-4 is obtained by directed evolution screening in the laboratory, which tolerates a minimum pH of 2.44. The mutant strain MTPfo-4, tolerant to multiple organic acids, has an increased tolerance to exogenous malic acid of up to 86.6 g/L. The mutant strain MTPfo-4 obtained is further identified. The mutant strain grows stably and well, and can tolerate a variety of organic acids (lactic acid, malic acid, succinic acid, fumaric acid, citric acid, gluconic acid, and tartaric acid). It also has a strong tolerance to inorganic acids (HCl and $H_3PO_4$). This is difficult to achieve in the existing research and reports of *S. cerevisiae*. The strain is intended to be used as an acid-tolerant chassis cell factory for producing various short-chain organic acids.

7 Claims, 4 Drawing Sheets

ACID-TOLERANT *SACCHAROMYCES CEREVISIAE* AND USE THEREOF

This application claims priority to Chinese Patent Application No. 202010631510.4, filed on Jul. 3, 2020, which is incorporated by reference for all purposes as if fully set forth herein.

FIELD OF THE INVENTION

The present invention relates to the technical field of microbial technology, and more particularly to an acid-tolerant *Saccharomyces cerevisiae* and use thereof.

DESCRIPTION OF THE RELATED ART

Short-chain organic acids, as natural metabolites of microorganisms, have been widely used in food, biomedicine, cosmetics, detergent, polymer and textile industries in recent years. Microbially produced short-chain organic acids mainly include propionic acid, pyruvic acid, lactic acid, 3-hydroxypropionic acid, intermediate metabolite α-ketoglutaric acid in tricarboxylic acid (TCA) cycle, malic acid, succinic acid, fumaric acid and citric acid. The calcium salt, sodium salt and ammonium salt of propionic acid have potent antiseptic ability and can be used as a preservative in animal feed and human food. Itaconic acid can be used to prepare synthetic fibers, synthetic resins and plastics, and its ester derivatives can be used as a plasticizer for styrene or polyvinyl chloride. As an important component of natural fruit juice, malic acid has a soft taste (with a high buffer index) and a special fragrance, causes no damage to the oral cavity and teeth, is metabolically beneficial to amino acid absorption, and causes no accumulation of fat, thus being a new generation of food acidulant. It is considered as "the most desirable food acidulant" in the biological and nutrition circles. Citric acid is multifunctional and non-toxic. It is recognized as a safe food additive by the committee of experts of FAO/WHO (Food and Agriculture Organization of the United Nations/World Health Organization), and is known as the first edible acidulant. Citric acid is used in the beverage industry and fermented alcoholic drinks. Not only can it impart a fruit flavor to the product, but it also has the effects of solubilization, buffering, and anti-oxidation, so that the pigment, aroma, carbohydrates and other ingredients are blended and compatible to form a harmonious taste and aroma, and at the same time the anti-microbial antiseptic effect is improved.

A GRAS strain of *Saccharomyces cerevisiae* can be used as a good platform in metabolic engineering to produce a variety of organic acid products, such as pyruvate, lactic acid, malic acid, succinic acid, fumaric acid and itaconic acid. In *S. cerevisiae*, two regulatory genes, that is, tHI2 and tHI3, are involved in the biosynthesis of thiamine. When the two genes are damaged, the mutants FMME-002ΔTHI2 and FMME-002ΔHI3 can be used for the production of pyruvic acid. The productivity of pyruvate salt with FMME-002ΔHI2 is high, and when 0.04 mM thiamine is added, the concentration of pyruvic acid is 8.21 g/L. To construct a high-producing strain of fumaric acid, the fumarase is knocked out by the researchers and the gene pyc (pyruvate carboxylase) from *Aspergillus oryzae* is expressed. Finally, the yield of fumaric acid by the engineered strain of *S. cerevisiae* is 5.64 g/L. During the synthesis of itaconic acid, the three genes ade3, bna2 and tes1 in *S. cerevisiae* are knocked out, and the final titer is 0.168 g/L after fermentation at a high density. The currently reported production of short-chain organic acids by *S. cerevisiae* is generally low, and is difficult to reach the level of industrial production considering the market economic benefits.

Environmental pH is a fundamental signal that affects cell metabolism and behavior. Therefore, for engineered cells, it is crucial to design and construct chassis cells in response to different environmental pH and have increasingly complex metabolic regulatory functions. In *S. cerevisiae*, the CCW14 promoter is studied systematically. CCW14 is a cell wall glycoprotein that can be activated by the CWI pathway under the stress of citric acid (pH 3.5) to improve the acid tolerance of host cells. Further stress-inducible synthesis is conducted by the researchers on this promoter, and a series of synthetic promoters are obtained. Finally, the mutant CCW14v5 with strong tolerance was screened. This promoter improves the acid tolerance of the cells compared with the natural promoter TEF1. Also, the lactic acid dehydrogenase gene (ldhL) derived from *Lactobacillus plantarum* is expressed at pH 3.0 to produce lactic acid. The ldhL strain (having a lactic acid titer of about 2.9-7.9 g/L) under control of the synthetic pH-inducible promoter is superior to the ldhL strain (having a yield of lactic acid of 0.72 g/L) under control of the natural promoter TEF1.

In the industrial production, the manufacturers have higher requirements for the production of organic acids considering the economic benefits. However, in the process of host cell construction, with the continuous accumulation of organic acids, a low-pH environment is formed, which causes a high inhibition on the growth of host cells. It is reported that during the fermentation to produce propionic acid, when the concentration reaches 10 g/L, the maximum limit is caused. In addition, the low pH formed by short-chain organic acids such as pyruvic acid, 3-hydroxypropionic acid, lactic acid, malic acid, and citric acid during the fermentation process have a potent inhibitory effect on the growth of host cells.

The currently reported microbial production of short-chain organic acids mainly involves the addition of a neutralizer ($CaCO_3$) to adjust the low pH during the fermentation. The resulting product mainly exists in the form of organic acid salts, which needs to be subsequently acidolyzed before further separation and purification. On the one hand, the cost and procedures for product separation and purification are added. On the other hand, if the neutralizer added previously or the acid used in the subsequent acidolysis is reacted incompletely, waste of resources and environmental pollution are caused. Due to the strong stress resistance of the cells itself, the difficulty of constructing an acid-tolerant system is increased, or the developed acid-tolerant chassis cells can only be used for the production of one organic acid. The product spectrum is narrow and the system cannot be used in the production of a variety of organic acids.

SUMMARY OF THE INVENTION

In order to solve the above-mentioned problems that low pH inhibits the growth of host cells, and the neutralizers leads to the increase in cost, the extra separation and purification procedures as well as environmental pollution, exogenous malic acid is added and used as a screening stress to iteratively evolve *Saccharomyces cerevisiae* in the present invention to obtain a cost-effective non-neutralizing fermentation host strain, so that the problems associated with the growth of *Saccharomyces cerevisiae* at a low pH and the production of short-chain organic acids. The main purpose of the present invention is to improve the acid tolerance of Saccharomyces cerevisiae and construct an acid-tolerant chassis cell factory of Saccharomyces cerevisiae for the production of various short-chain organic acids.

A first object of the present invention is to provide an acid-tolerant Saccharomyces cerevisiae strain, designated as Saccharomyces cerevisiae MTPfo-4, which was deposited in the China Center for Type Culture Collection with Accession No.: CCTCC M 2020199 on Jun. 10, 2020 (Address: Wuhan University, Wuhan).

Preferably, the lowest pH tolerated by the Saccharomyces cerevisiae is 2.44.

Preferably, the tolerance of Saccharomyces cerevisiae to exogenous malic acid reaches 86.6 g/L.

A second object of the present invention is to provide use of the Saccharomyces cerevisiae in the production of short-chain organic acids.

Preferably, the Saccharomyces cerevisiae is used as a chassis cell to construct a strain for producing a short-chain organic acid.

Preferably, the short-chain organic acid is selected from the group consisting of pyruvic acid, 3-hydroxypropionic acid, lactic acid, malic acid, succinic acid, fumaric acid, citric acid, gluconic acid, tartaric acid, and furoic acid.

A third object of the present invention is to provide a microbial agent containing the Saccharomyces cerevisiae.

Preferably, the microbial agent is a solid agent.

Preferably, the microbial agent is a liquid agent.

As compared with the prior art, the present invention has the following beneficial effects.

In the present invention, by using exogenously added short-chain organic malic acid as a stress, an acid-tolerant mutant S. cerevisiae strain MTPfo-4 is obtained by directed evolution screening in the laboratory, which can tolerate a minimum pH of 2.44 that is also the currently reported lowest pH tolerated by Saccharomyces cerevisiae. The mutant strain MTPfo-4, which can tolerate multiple organic acids, has an increased tolerance to exogenous malic acid of up to 86.6 g/L. The mutant strain MTPfo-4 obtained is further identified. The mutant strain grows stably and well, and can tolerate a variety of organic acids (lactic acid, malic acid, succinic acid, fumaric acid, citric acid, gluconic acid, and tartaric acid). In addition, it also has a strong tolerance to inorganic acids (HCl and $H_3PO_4$. This is difficult to achieve in the known research and reports of S. cerevisiae. The strain is intended to be used as an acid-tolerant chassis cell factory for the production of a variety of short-chain organic acids.

Deposit of Biological Material:

Saccharomyces cerevisiae MTPfo-4 was deposited in the China Center for Type Culture Collection with Accession No.: CCTCC M 2020199 on Jun. 10, 2020 (Address: Wuhan University, Wuhan).

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Example 1

Evolution and Screening of Acid-Tolerant Saccharomyces cerevisiae

Starting with Saccharomyces cerevisiae CEN.PD2-1C, a mutant Saccharomyces cerevisiae strain with a tolerance to lower pH was obtained by directed evolution screening by exogenously adding different concentrations of malic acid. In the present invention, by adding different concentrations of malic acid, the pH was controlled to decrease step by step (starting from pH 6.0 at which the addition amount of exogenous malic acid was 4.6 g/L). After the cells were evolved to be able to grow at a pH level, the cells were cultured at this level for enrichment (the goal is that the $OD_{600}$ of the cells at this pH is stable for 48 h, and has no significant increase between two subcultures; and the purpose is to increase the number of mutant cells and make cell growth more stable at this pH), and then evolved at a next pH level. From the initial pH 6.0 to pH 4.0, each pH span is 0.2, that is, 6.0, 5.8, 5.6 . . . 4.2, and 4.0. From pH 4.0 to pH 3.5, each pH span is 0.1, that is, 4.0, 3.9, 3.8 . . . 3.6, and 3.5. From pH 3.5 to pH 3.0, each pH span is 0.05, that is, 3.5, 3.45, 3.4 . . . 3.05, and 3.0. From pH 3.0 to pH 2.8, each pH span is 0.02, that is, 3.0, 2.98, 2.96 . . . 2.82, and 2.80. When the pH is below 2.8, each pH span is 0.01, that is, 2.8, 2.79, 2.78 . . . 2.45, and 2.44. The cells grow faster from the initial pH 6.0 to pH 4.0, and it may be possible to directly evolve from pH 4.0. However, in order to obtain a more stable acid-tolerant strain, iterative evolution from pH 6.0 is recommended in the present invention. The evolved strain obtained at each level of pH will be used as the starting strain for the next passage until a mutant that tolerates a lower pH is evolved.

Figure 1:
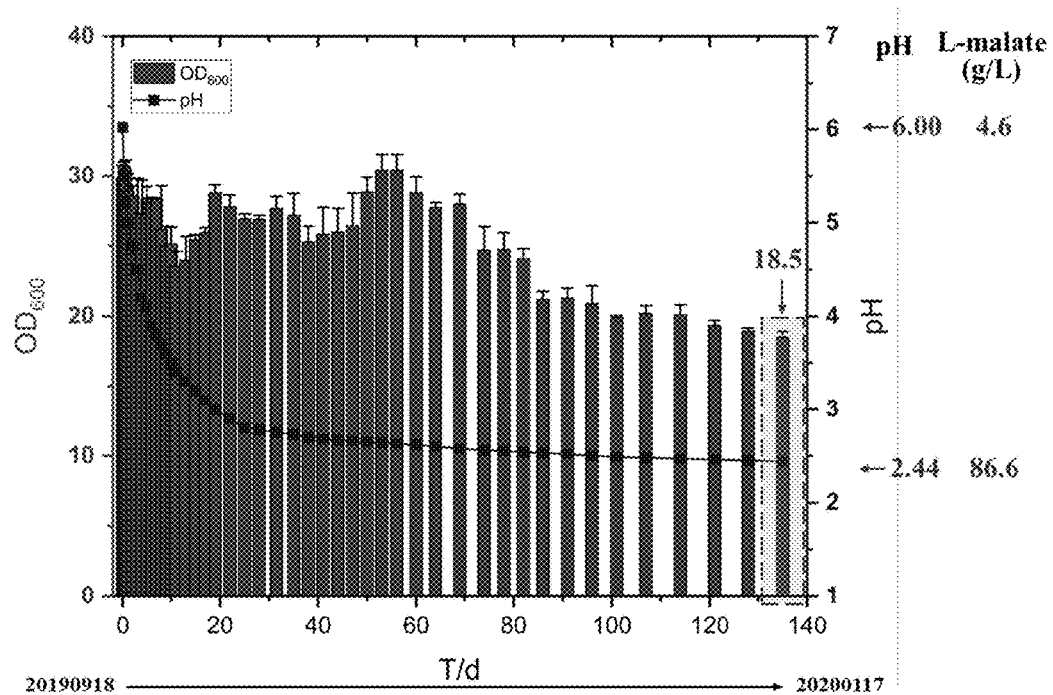
FIG. 1 shows the evolution and screening of acid-tolerant Saccharomyces cerevisiae.

As shown in FIG. 1, after nearly four months of continuous directed evolution, a mutant MTPfo-4 that can tolerate 86.6 g/L malic acid (pH 2.44) was screened. After 48 hours of culture at each level of pH, the pH of the medium remains stable, and there is no increase, but a tendency to decrease. For example, after the mutant MTPfo-4 is cultured at pH 2.44 for 48 h, the pH is stabilized at 2.42-2.44.

At pH 2.44, the $OD_{600}$ reaches 18.5 after 48 h of culture. The results show that the mutant strain can grow stably. This is also the currently reported lowest pH that S. cerevisiae can tolerate.

The screened mutant Saccharomyces cerevisiae MTPfo-4 was deposited in the China Center for Type Culture Collection with Accession No.: CCTCC M 2020199 on Jun. 10, 2020 (Address: Wuhan University, Wuhan).

Example 2

Cell Trait Analysis of Acid-Tolerant Saccharomyces cerevisiae

Figure 2:
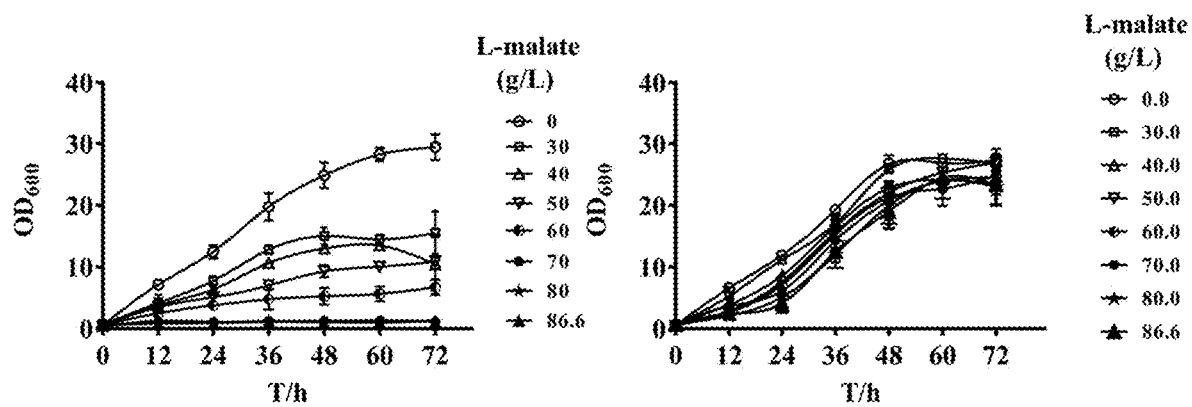
FIG. 2 shows the growth curves of Saccharomyces cerevisiae and its mutant under malic acid stress.

To verify the stability of the obtained mutant S. cerevisiae strain MTPfo-4 at a low pH, the growth of MTPfo-4 and the starting strain CEN.PD2-1C were compared with the addition of different amounts of exogenous malic acid. The concentration (g/L) of the added exogenous malic acid is 0, 30, 40, 50, 60, 70, 80, 90, and 100. The cells were sampled every 12 h for consecutive 72 h. The growth curve of the strain was determined. The determination result is shown in FIG. 2. Compared with the starting strain CEN.PD2-1C, the mutant MTPfo-4 grows greatly in the presence of the exogenously added malic acid and has a strong tolerance to the exogenously added malic acid.

Example 3

Analysis of Tolerance of Acid-Tolerant Saccharomyces cerevisiae to Other Acids

Figure 3:
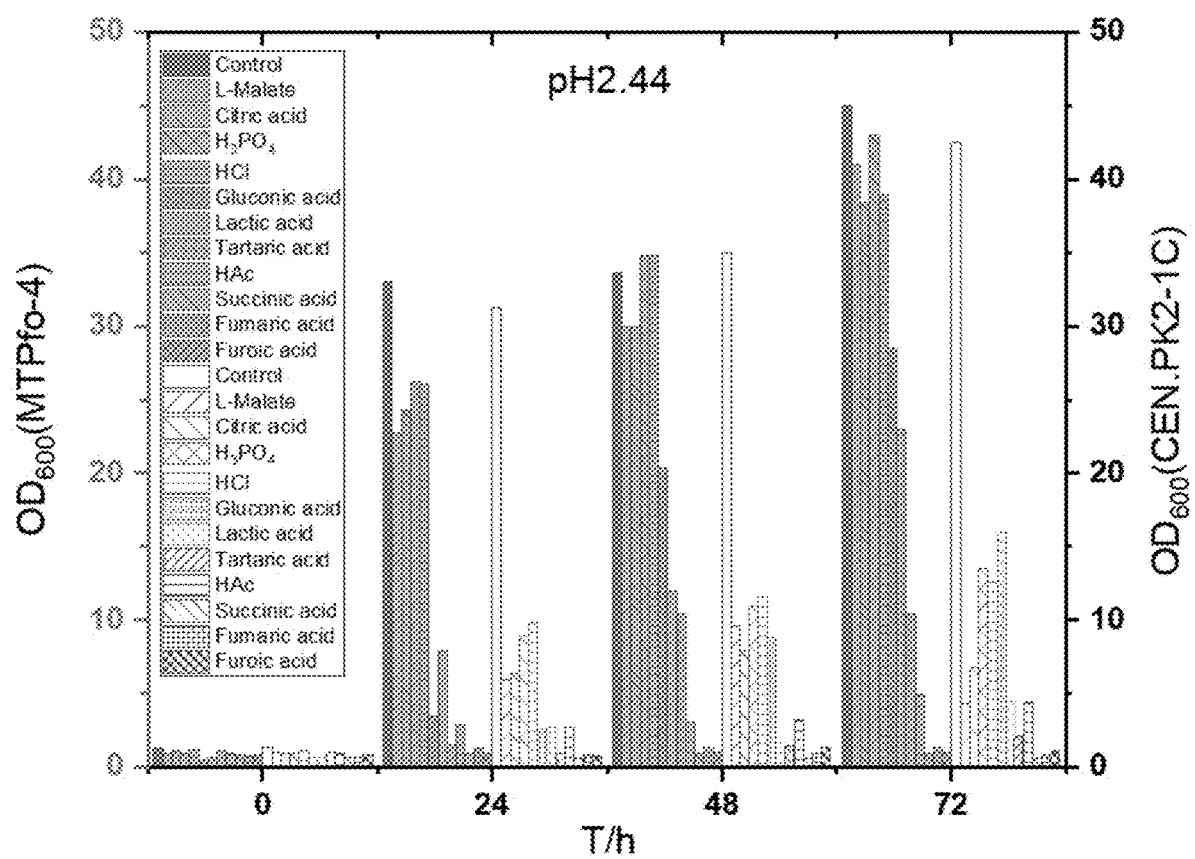
FIG. 3 shows the analysis of tolerance of the mutant MTPfo-4 to other acids (pH 2.44)
Figure 4:
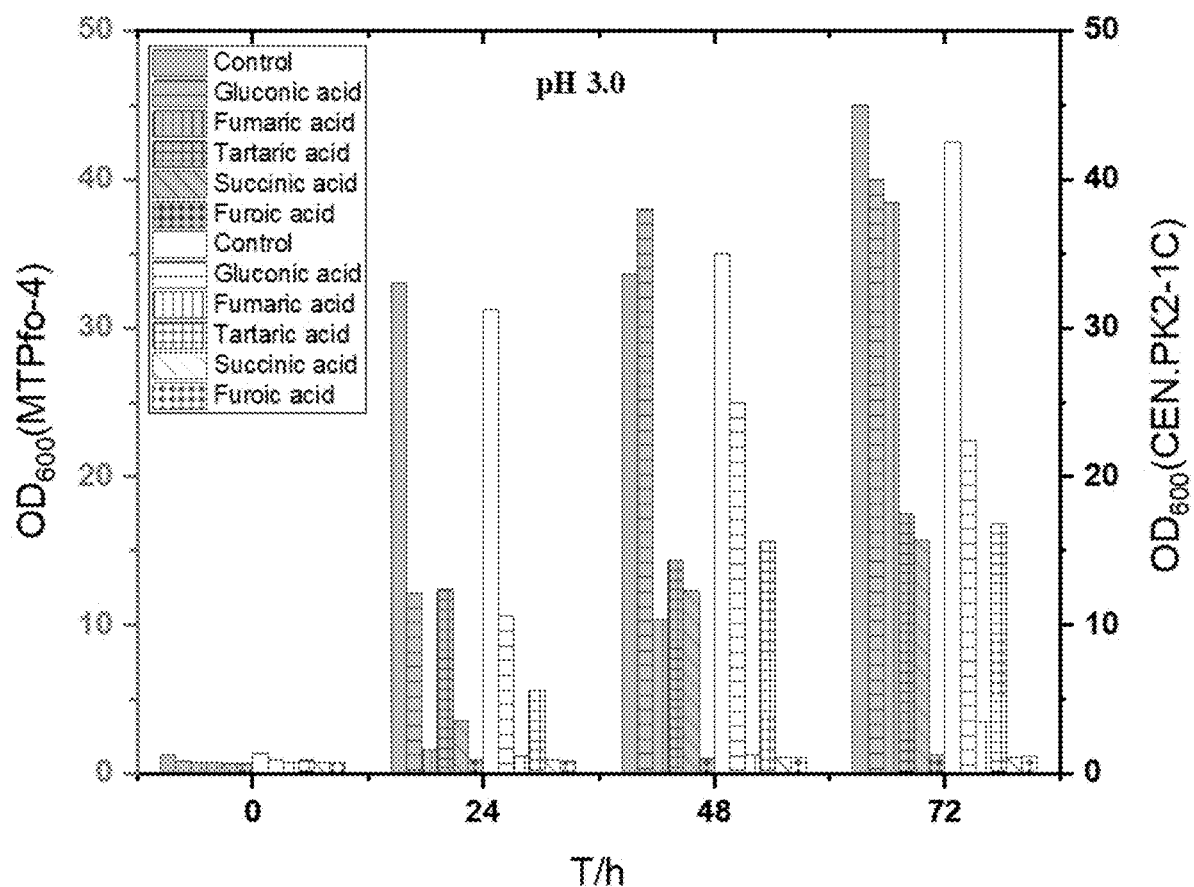
FIG. 4 shows the analysis of tolerance of the mutant MTPfo-4 to other acids (pH 3.0).

To analyze the tolerance of the mutant MTPfo-4 to other acids, 10 acids, including 2 inorganic acids of HCl and $H_3PO_4$, and 8 organic acids of lactic acid, malic acid, fumaric acid, succinate acid, tartaric acid, furoic acid, gluconic acid, and citric acid, were added exogenously in the present invention to analyze the acid tolerance of cells. The initial pH was controlled to 2.44. The cells were sampled every 12 h for consecutive 72 h. The acid tolerance of cells was analyzed by determining the $OD_{600}$. The results are shown in FIG. 3. Compared with the starting strain CEN.PD2-1C, MTPfo-4 has a stronger tolerance to the 6 acids including HCl, $H_3O_4$, lactic acid, malic acid, citric acid, and gluconic acid. In contrast, at this pH, all 10 acids have a strong inhibitory effect on the growth of CEN.PD2-1C. Since fumaric acid, succinic acid, furoic acid, and tartaric acid also had an inhibitory effect on the mutant MTPfo-4 at pH 2.44, in the present invention, the initial pH of the four acids is adjusted to 3.0. The cells were sampled every 12 h for consecutive 72 h. The acid resistance of the cells was analyzed again by determining the $OD_{600}$. The results are shown in FIG. 4. Compared with the starting strain CEN.PD2-1C, MTPfo-4 has a stronger tolerance to the four acids. Similarly, at this pH, all four acids have a strong inhibitory effect on the growth of CEN.PD2-1C.

Example 4

Analysis of Metabolic Substance of Acid-Tolerant Saccharomyces cerevisiae

Figure 5:
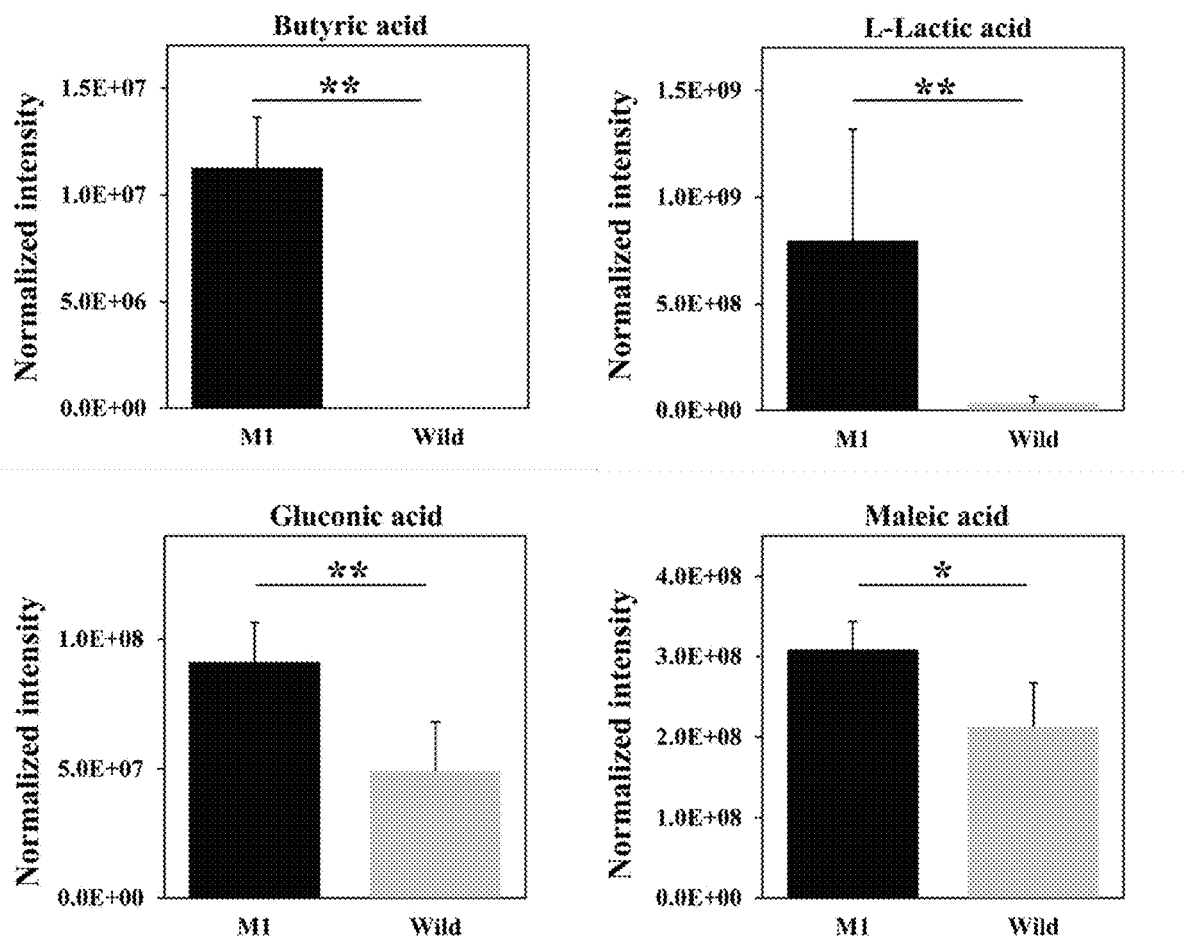
FIG. 5 shows the analysis of metabolic substance of the mutant MTPfo-4.

In order to analyze the advantages of the acid-tolerant Saccharomyces cerevisiae mutant MTPfo-4 as chassis cells, metabolomics analysis is performed on MTPfo-4 in the present invention. As compared with the starting strain CEN.PD2-1C, a variety of metabolites are affected for the mutant MTPfo-4, and the effects on the short-chain organic acids are mainly analyzed in the invention. As shown in FIG. 5, L-Lactic acid, Butyric acid, Gluconic acid and Maleic acid in the metabolites of mutant MTPfo-4 are increased significantly comparing with the starting strain (*: $P \leq 0.05$; **: $P \leq 0.01$).

Example 5

Figure 6:
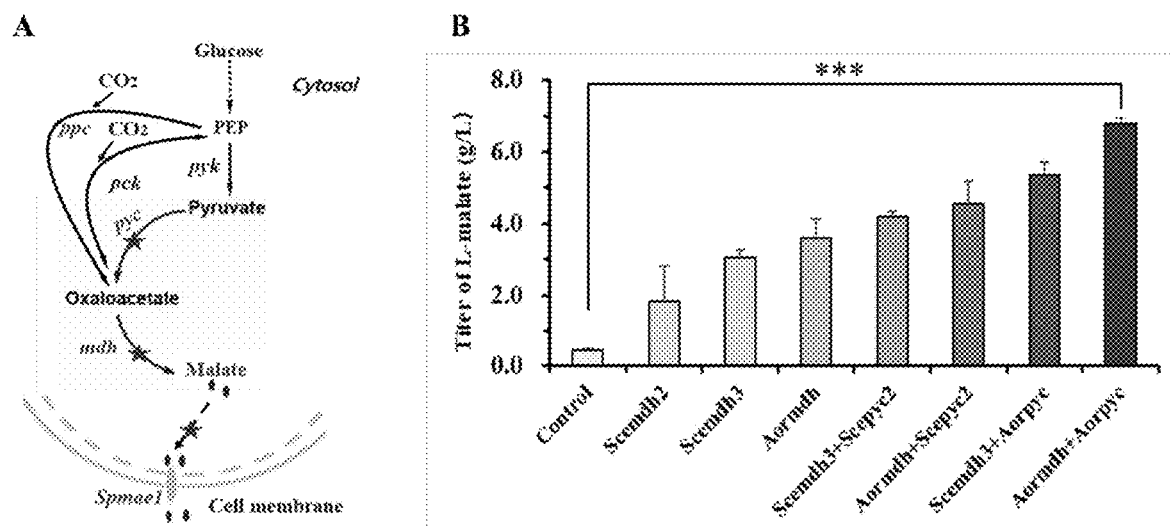
FIG. 6 shows the use of the mutant MTPfo-4 in production of short-chain organic acids.

Synthesis of Organic Acids by Metabolic Modification of Acid-Tolerant Saccharomyces cerevisiae In order to better verify the potential of mutant MTPfo-4 as chassis cells to produce organic acids, the target product is synthesized by metabolic modification in the invention, for example malic acid. The synthesis pathway of malic acid in Saccharomyces cerevisiae is shown in FIG. 6A, the key gene mdh (malate dehydrogenase, selecting endogenous genes Scemdh2 and Scemdh3, the exogenous gene Aormdh being derived from Aspergillus oryzae) and pyc (pyruvate carboxylase, selecting endogenous gene Scepyc2, the exogenous gene Aorpyc being derived from Aspergillus oryzae) are integrated. First, the mdh genes of different sources are integrated and fermented in a 250 mL shake flask with a loaded liquid of 30 mL, and the fermentation medium includes glucose 20 g/L, tryptone 20 g/L, and yeast powder 10 g/L. Then the flask was cultured under 30° C. at 220 r/min for 72 h. At the end of fermentation, the yield of malic acid in the supernatant is determined by HPLC (High Performance Liquid Chromatography). 1-2 mL of fermentation broth is taken for centrifugation at 12000 rpm for 15-20 min, then the supernatant is collected to determine by HPLC the extracellular concentration of malic acid. The determination results of malic acid by HPLC in the fermentation broth are shown in FIG. 6B. As compared with the yield of 0.45 g/L for the control strain (MTPfo-4 before modification), by overexpression of mdh2, mdh3 and Aormdh, the yields of malic acid are 1.83 g/L, 3.05 g/L and 3.59 g/L respectively.

Based on the significantly increased production of malic acid by overexpression of mdh3 and Aormdh, Scepyc2 and Aorpyc are overexpressed to obtain four different combinations of Scemdh3+Scepyc2, Aormdh+Scepyc2, Scemdh3+Aorpyc and Aormdh+Aorpyc. Fermentation is performed in a 250 mL of shake flask with a loaded liquid of 30 mL, the fermentation medium includes glucose 20 g/L, tryptone 20 g/L, and yeast powder 10 g/L. Then the flask was cultured under 30° C. at 220 r/min for 72 h. At the end of fermentation, the yield of malic acid in the supernatant is determined by HPLC (High Performance Liquid Chromatography). 1-2 mL of fermentation broth is taken for centrifugation at 12000 rpm for 15-20 min, and then the supernatant is collected to determine by HPLC the extracellular concentration of malic acid. The determination results of malic acid by HPLC in the fermentation broth are shown in FIG. 6B. As compared with the control strain (MTPfo-4 before modification), by overexpression of Scemdh3+Scepyc2, Aormdh+Scepyc2, Scemdh3+Aorpyc and Aormdh+Aorpyc, the yields of malic acid are 4.2 g/L, 4.55 g/L, 5.35 g/L and 6.8 g/L respectively. The above results show that, the extracellular production of overexpressed Aormdh+Aorpyc is 15.1 times higher than that of the starting strain.

All the above results show that, the mutant strain MTPfo-4 has a has strong tolerance to various acids, and has the potential to produce a variety of organic acids as acid-resistant chassis cells, and thus can be further developed for the production of a variety of short-chain organic acids.

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:
1. An acid-tolerant Saccharomyces cerevisiae, which is designated as Saccharomyces cerevisiae MTPfo-4 and deposited in the China Center for Type Culture Collection with Accession No.: CCTCC M 2020199 on Jun. 10, 2020 (Address: Wuhan University, Wuhan).

2. The *Saccharomyces cerevisiae* according to claim 1, wherein the lowest pH tolerated by the *Saccharomyces cerevisiae* is 2.44.

3. The *Saccharomyces cerevisiae* according to claim 1, wherein the tolerance of *Saccharomyces cerevisiae* to exogenous malic acid reaches 86.6 g/L.

4. The *Saccharomyces cerevisiae* according to claim 1, wherein the *Saccharomyces cerevisiae* tolerates lactic acid, malic acid, succinic acid, fumaric acid, citric acid, gluconic acid, tartaric acid, HCl, and $H_3PO_4$.

5. A microbial agent, comprising the *Saccharomyces cerevisiae* according to claim 1.

6. The microbial agent according to claim 5, wherein the microbial agent is a solid agent.

7. The microbial agent according to claim 5, wherein the microbial agent is a liquid agent.

\* \* \* \* \*